United States Patent
Falahee et al.

(10) Patent No.: US 7,563,275 B2
(45) Date of Patent: Jul. 21, 2009

(54) BONE FIXATION IMPLANT SYSTEM AND METHOD

(75) Inventors: Mark H. Falahee, Ann Arbor, MI (US); Leonel Dominguez, Jacksonville, FL (US); John R. Pepper, Cheshire, CT (US); Ian McDermott, New London, PA (US); K. Arjun Joseph, Bensalem, PA (US); James Hooper, Deptford, NJ (US)

(73) Assignee: U.S. Spinal Technologies, LLC

( * ) Notice: Subject to any disclaimer, the term of this patent is extended or adjusted under 35 U.S.C. 154(b) by 482 days.

(21) Appl. No.: 10/973,524

(22) Filed: Oct. 26, 2004

(65) Prior Publication Data

US 2005/0234459 A1     Oct. 20, 2005

(51) Int. Cl.
*A61B 17/84* (2006.01)
*A61F 2/08* (2006.01)
*A61B 17/60* (2006.01)

(52) U.S. Cl. ........................... 606/328; 606/104

(58) Field of Classification Search ............. 606/69–73, 606/99, 86, 104; 81/13, 44, 57, 456; 227/19, 227/30, 34, 35
See application file for complete search history.

(56) References Cited

U.S. PATENT DOCUMENTS

| | | | | |
|---|---|---|---|---|
| 3,178,971 A * | 4/1965 | Bachli et al. ................ | 81/125 |
| 3,545,444 A * | 12/1970 | Green ......................... | 606/143 |
| 3,822,818 A * | 7/1974 | Strekopytov et al. ........ | 227/124 |
| 5,234,431 A * | 8/1993 | Keller ......................... | 606/70 |
| 5,527,312 A | 6/1996 | Ray | |
| 5,558,674 A | 9/1996 | Heggeness et al. | |
| 5,649,931 A * | 7/1997 | Bryant et al. ................ | 606/104 |
| 5,690,632 A * | 11/1997 | Schwartz et al. ............. | 606/73 |
| 5,720,751 A * | 2/1998 | Jackson ...................... | 606/86 |
| 5,735,850 A * | 4/1998 | Baumgartner et al. ........ | 606/61 |
| 6,050,997 A * | 4/2000 | Mullane ...................... | 606/61 |
| 6,146,383 A * | 11/2000 | Studer et al. ................. | 606/61 |
| 6,368,319 B1 * | 4/2002 | Schaefer ...................... | 606/60 |
| 6,485,518 B1 | 11/2002 | Cornwall et al. | |
| 6,540,747 B1 | 4/2003 | Marino | |
| 6,623,485 B2 * | 9/2003 | Doubler et al. ............... | 606/61 |
| 6,648,893 B2 | 11/2003 | Dudasik | |

(Continued)

*Primary Examiner*—Anu Ramana
(74) *Attorney, Agent, or Firm*—Gifford, Krass, Sprinkle, Anderson & Citkowski, P.C.

(57) ABSTRACT

A system for performing bone arthrodesis includes an implant for bone arthrodesis and a bone fastening device. The implant includes a fastener with an elongated shaft having a head at one end and a bone-piercing point at the opposite end. A first washer has structure for engaging the head of the shaft so as to be polyaxially pivotable with respect to the head. A locking member has structure for engaging the shaft. The locking member can have a second washer pivotally engaged thereto. The bone fastening device can include an elongated cannula with a collet for detachably engaging the first washer and for advancing the first washer. Structure is provided for engaging the fastener and for advancing and rotating the fastener through the collet and through the first washer. The bone arthrodesis device further includes a lower end portion extending from the cannula. The lower end portion has structure for detachably engaging the locking member. The fastener, first washer, and locking member are aligned such that the advancing fastener will advance through the first washer, drill through the bone, and move into the locking member. A method for performing bone arthrodesis is also disclosed.

6 Claims, 13 Drawing Sheets

U.S. PATENT DOCUMENTS

| | | |
|---|---|---|
| 6,669,698 B1 | 12/2003 | Tromanhauser et al. |
| 6,811,567 B2 | 11/2004 | Reiley |
| 6,949,123 B2 | 9/2005 | Reiley |
| 6,966,930 B2 | 11/2005 | Arnin et al. |
| 7,041,136 B2 | 5/2006 | Goble et al. |
| 2004/0111093 A1 | 6/2004 | Chappuis |
| 2004/0225360 A1 | 11/2004 | Malone |
| 2004/0254575 A1 | 12/2004 | Obenchain et al. |
| 2005/0124993 A1 | 6/2005 | Chappuis |
| 2005/0149030 A1 | 7/2005 | Serhan et al. |
| 2005/0273110 A1 | 12/2005 | Boehm, Jr. et al. |
| 2006/0004367 A1 | 1/2006 | Alamin et al. |
| 2006/0111779 A1 | 5/2006 | Petersen |
| 2006/0111780 A1 | 5/2006 | Petersen |

* cited by examiner

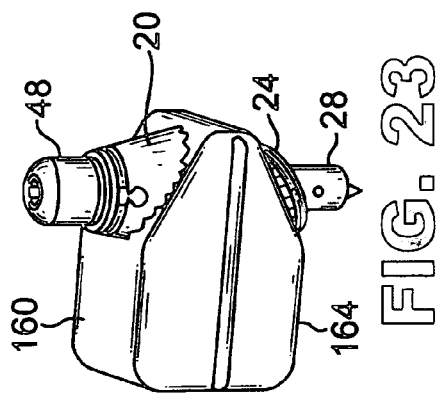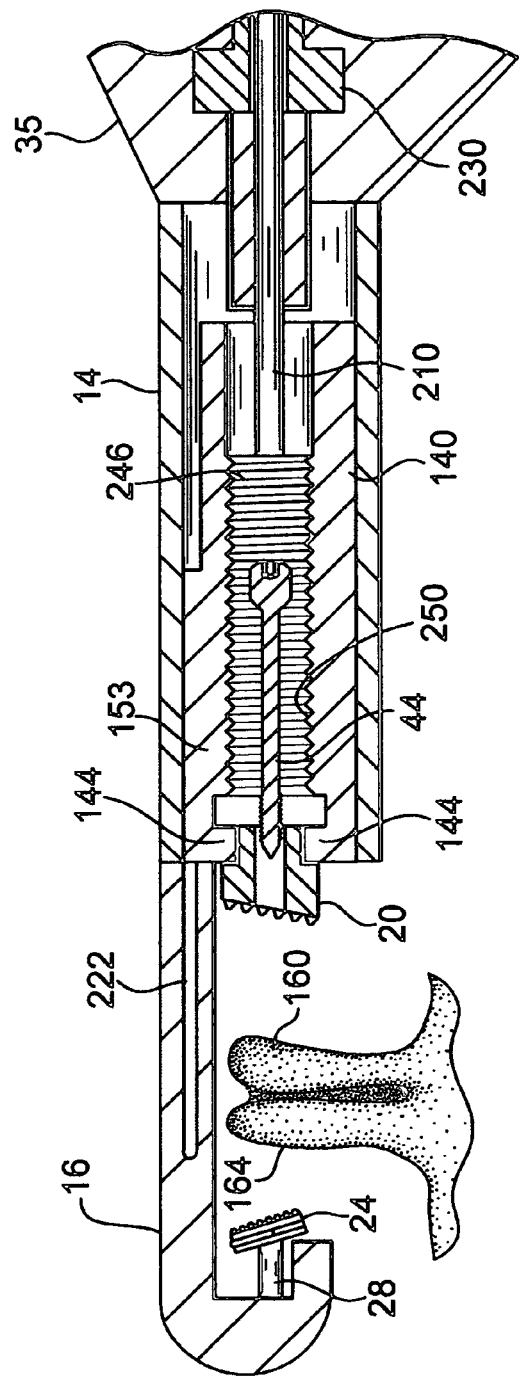

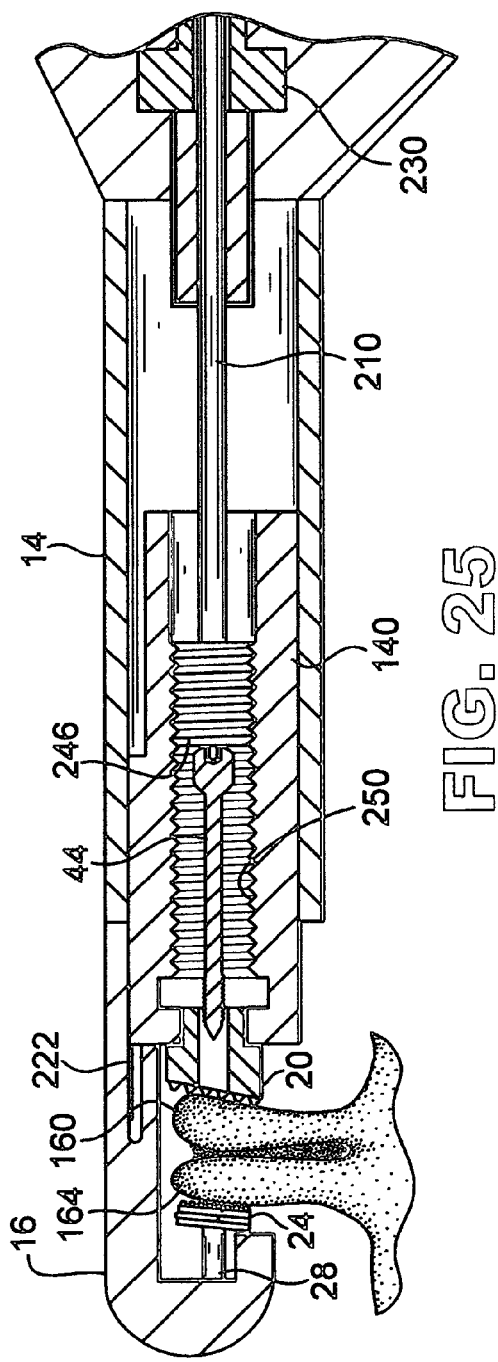
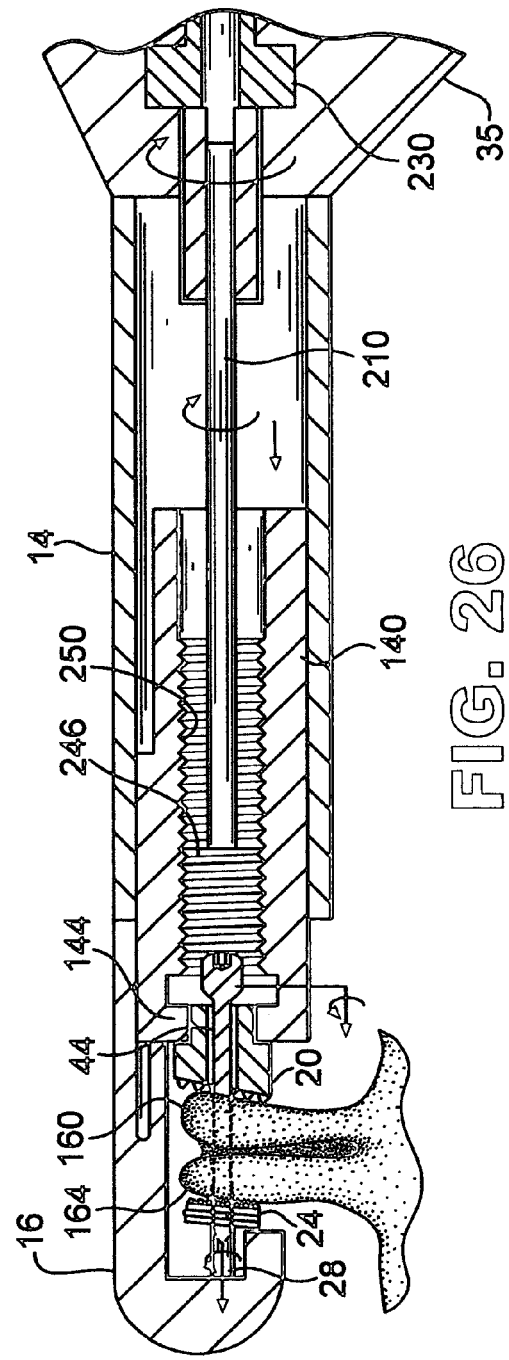

BONE FIXATION IMPLANT SYSTEM AND METHOD

CROSS-REFERENCE TO RELATED APPLICATIONS

This application claims the benefit of U.S. Utility patent application Ser. No. 10/683,076, filed Oct. 10, 2003, which claims the benefit of U.S. Provisional Application No. 60/417,543, filed Oct. 10, 2002.

FIELD OF THE INVENTION

This invention relates to bone arthrodesis, and more particularly to bone fixation implants and systems and methods for installing such implants.

BACKGROUND OF THE INVENTION

Bone arthrodesis or fusion is a process used to assist in the healing or stabilization of impaired bones or joints. In particular, facet arthrodesis is used to fuse the superior and inferior facet in spinal treatment operations. Prior art systems and methods have used bone screws which are screwed through the superior and inferior facets to immobilize the joint so as to permit the adjoined bone sections to fuse together. Wire has also been used to loop around the facets to immobilize the joint. The surgical procedures that must be performed to implant the screws or wires are difficult and time consuming. There is therefore a need for improved bone fixation implants, devices and methods.

SUMMARY OF THE INVENTION

An implant for bone fixation comprises a fastener with an elongated shaft having a head at one end and a bone-piercing point at the opposite end. A first washer has structure for engaging the head of the shaft so as to be polyaxially pivotable with respect to the head. A locking member has structure for engaging the shaft. The locking member has a second washer pivotally engaged thereto. The shaft and the locking member can have cooperating threads. The locking member can be a nut. The second washer can be pivotally attached to the nut by a clip.

The first washer and second washer can comprise angled contact surfaces. The contact surfaces can be serrated. One of the head and the first washer can have a convex surface. The other of the head and the first washer can have a cooperating concave surface. The convex surface is in contact with the concave surface to provide for polyaxial pivoting of the first washer with respect to the head. The first washer can comprise structure for engagement to a bone fastening device. The structure can comprise a circumferential groove that is adapted to receive a flange on the fastening device. The first washer can comprise rotational engagement structure. The rotational engagement structure can comprise depressions adapted to receive protrusions on a fastening device.

The locking member can comprise structure for engaging the fastening device. The structure can comprise depressions adapted to receive protrusions on a lower end portion of the fastening device.

A bone fastening device according to the invention can have an elongated cannula with a collet for detachably engaging a first washer and for advancing the first washer. The fastening device can further comprise structure for detachably engaging a fastener and for advancing the fastener through the collet and through the first washer. A lower end portion extends from the cannula. The lower end portion can have structure for detachably engaging a locking member. The fastener, first washer, and locking member are aligned such that the advancing fastener will advance through the first washer, through the bone, through the second washer and into the locking member.

A system for performing bone arthrodesis includes an implant for bone fixation and a bone fastening device. The implant includes an elongated shaft having a head at one end and a bone-piercing point at the opposite end. A first washer has structure for engaging the head of the shaft so as to be polyaxially pivotable with respect to the head. A locking member has structure for engaging the shaft. The locking member can have a second washer pivotally engaged thereto. The bone fastening device can include an elongated cannula with a collet for detachably engaging the first washer and for advancing the first washer. Structure is provided for detachably engaging the fastener and for advancing the fastener through the collet and through the first washer. The bone fastening device further includes a lower end portion extending from the cannula. The lower end portion has structure for detachably engaging the locking member. The fastener, first washer, and locking member are aligned such that the advancing fastener will advance through the first washer, through the bone, through the second washer and into the locking member.

A method for performing bone arthrodesis includes the steps of providing an implant for bone fixation, the implant comprising: a fastener with an elongated shaft having a head at one end and a bone-piercing point at the opposite end; a first washer having structure for engaging the head of the shaft so as to be polyaxially pivotable with respect to the head; and a locking member having structure for engaging the shaft. The locking member can have a second washer pivotally engaged thereto.

The method further includes the step of providing a bone fixation device, the bone fixation device comprising: an elongated cannula having a collet for detachably engaging the first washer and for advancing the first washer, and structure for engaging said fastener and for advancing the fastener through the collet and through the first washer; a lower end portion extending from said cannula, said lower end portion having structure for detachably engaging the locking member. The fastener, first washer, and locking member are aligned such that the advancing fastener will advance through the first washer, through the bone, through the second washer and into the locking member.

The method further includes the step of positioning the bone fixation device with the bone between the cannula and the lower end portion. The device is operated to advance the first washer to the bone. The device is then operated to advance the fastener through the first washer, the bone, and into the locking member.

BRIEF DESCRIPTION OF THE DRAWINGS

There is shown in the drawings embodiments which are presently preferred, it being understood, however, that the invention is not limited to the precise arrangements and instrumentalities shown, wherein:

FIG. 23 is a schematic perspective view showing bone fixation utilizing an implant according to the invention.

FIG. 24 is a schematic cross section illustrating a bone fixation system and method, in a fist mode of operation.

FIG. 25 is a schematic cross section illustrating a second mode of operation.

FIG. 26 is a schematic cross section illustrating a third mode of operation.

DETAILED DESCRIPTION OF THE INVENTION

Figure 1:
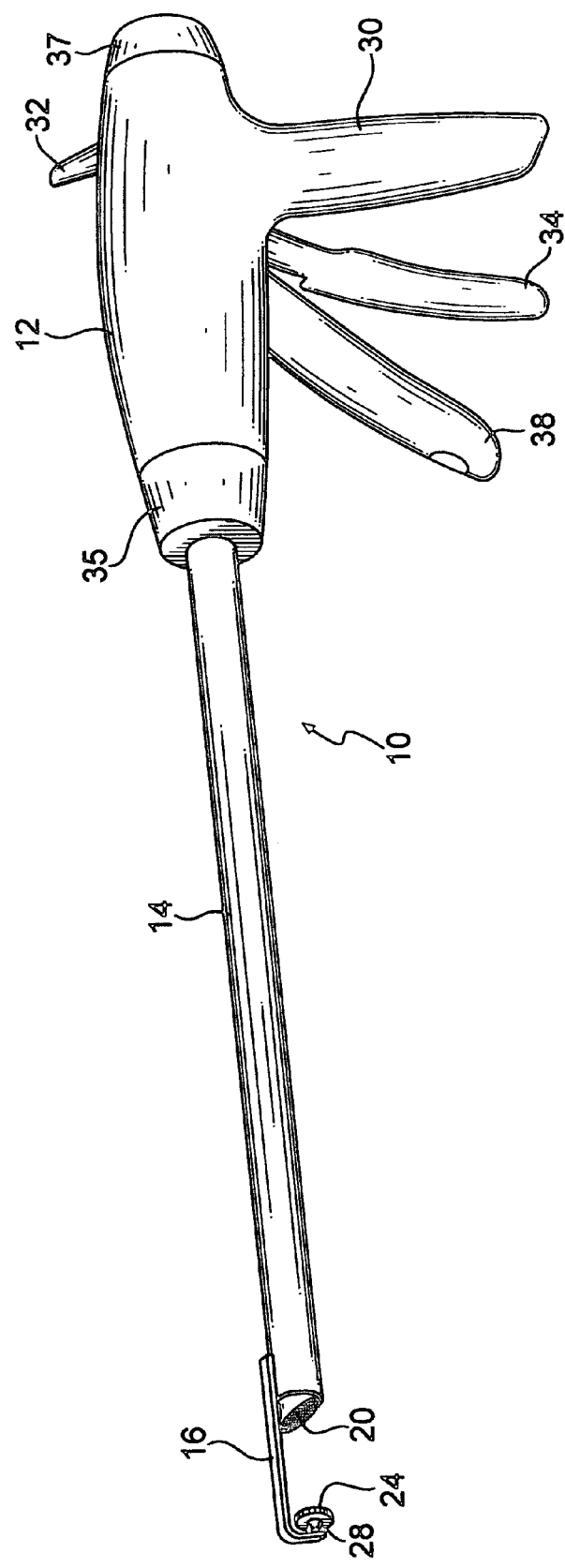
FIG. 1 is a perspective view of a bone fastening device according to the invention.

There is shown in FIG. 1 a bone fastening device 10 according to the invention. The device 10 has a main body 12 and an elongated housing 14 terminating in a lower end portion 16. The device 10 has structure for holding a first washer 20 at a distal portion of the elongated housing 14 and a second washer 24 and locking member 28 in the lower end portion 16. A handle 30 is provided to grip the device, and triggers 34 and 38 can be provided to operate the device during the implantation process. A guide knob 35 can be operated to rotate the housing 14 and attached lower end portion 16 to properly position the second washer 24. A locking lever 32 can be provided to lock the device 10 on the bone after the first washer 20 and second washer 24 have been properly positioned. The locking lever 32 may be unlocked to allow repositioning of first washer 20 and second washer 24. A knob 37 can be provided to manually advance the fastener and apply appropriate torque.

Figure 1A:
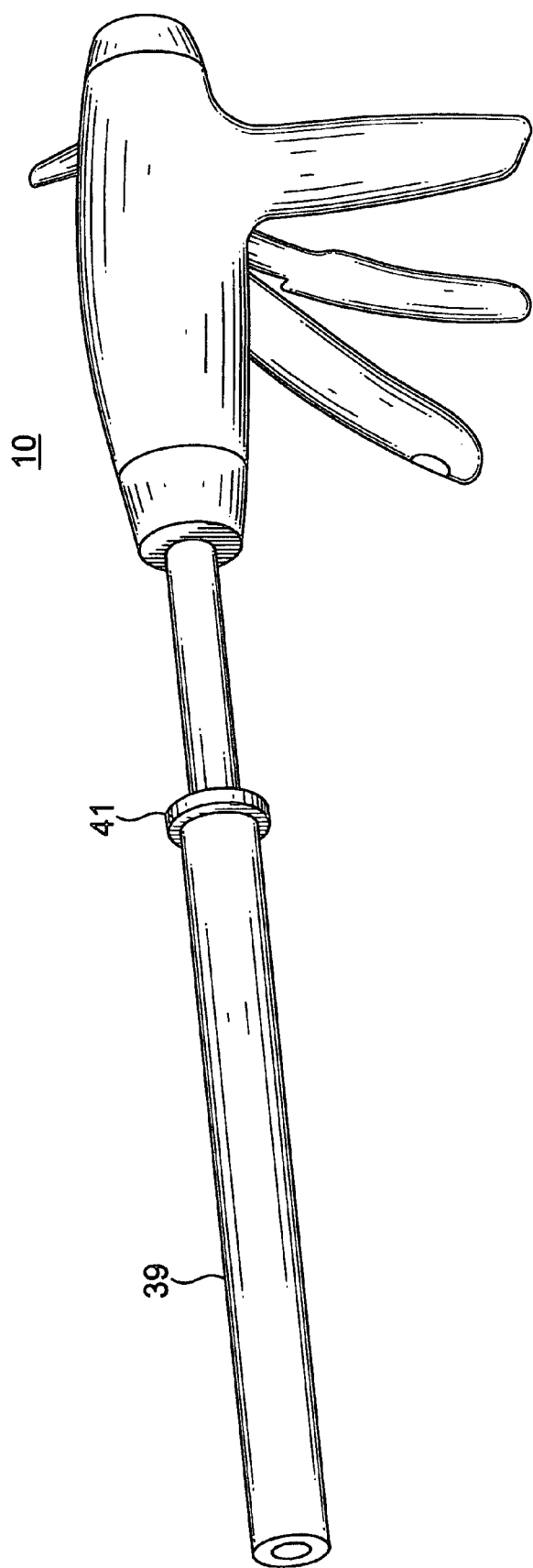
FIG. 1a is a perspective view of a bone fastening device having a protective cannula.

A slidable protective cannula or sheath 39 may be used to facilitate insertion into the body and cover lower end portion 16. In FIG. 1a there is shown a bone fastening device 10 having a protective cannula or sleeve 39 for shielding the housing 14 and lower end portion 16 during the insertion process. A grip 41 can be used to pull back the cannula 39 prior to use. The housing 14, lower end portion 16 and guide knob 35 can be detachable from the main body 12. Another housing 14, lower end portion 16 and guide knob 35, with another implant, can be attached for reuse of the main body portion 12.

Figure 2:
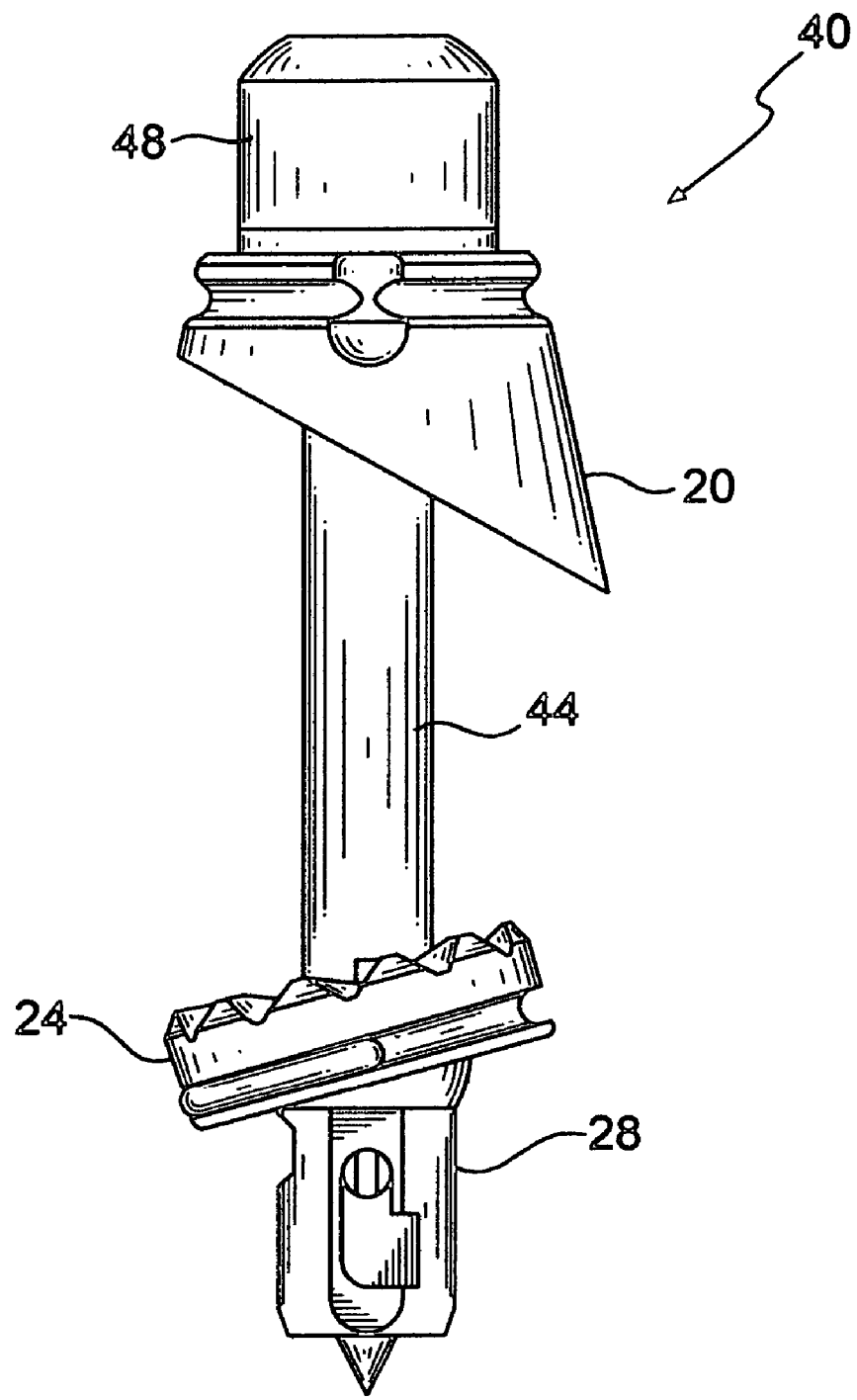
FIG. 2 is a side elevation of a bone arthrodesis implant according to the invention.
Figure 3:
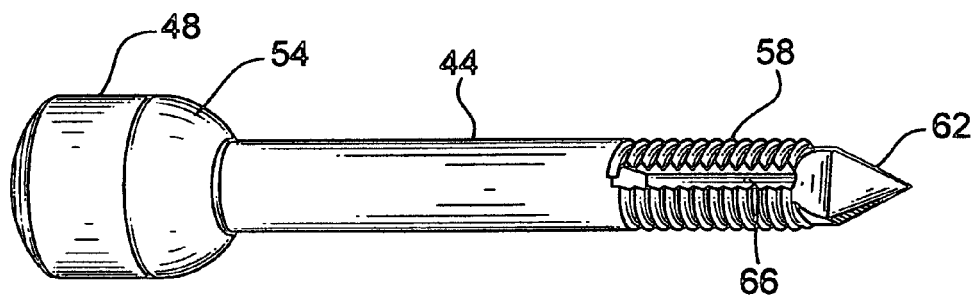
FIG. 3 is a side elevation of a fastener.
Figure 4:
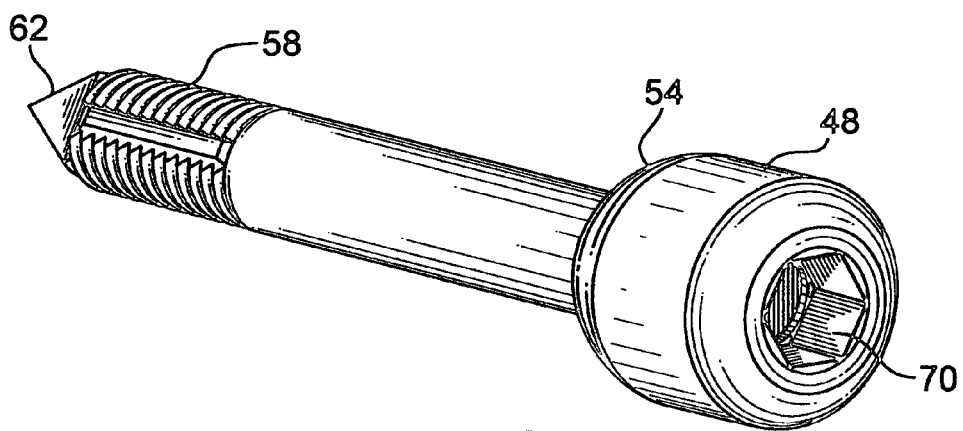
FIG. 4 is a perspective view.

There is shown in FIG. 2 an implant 40. The implant 40 comprises a fastener having an elongated shaft 44 and a head 48. The fastener engages the first washer 20 and the second washer 24 and locking member 28. As shown in FIG. 3, the head 48 can have a convex surface 54 for use in engaging the first washer 20 as will be described below. Threads 58 are provided on the shaft 44 for purposes of engaging the locking member 28. Other engagement structure is possible. A pointed end 62 is provided for piercing bone during the implantation process. Grooves or flutes 66 provide space for bone chips to disperse during insertion into locking member 28 and to carry bone debris away from the point 62 as it is progressing through the bone. Suitable structure such as hex opening 70 is provided for engagement of the fastener 44 to apply compressive and rotational forces during the implantation process. Depressions or other suitable structure can be provided to permit a fastening device to grip the head 48.

Figure 5:
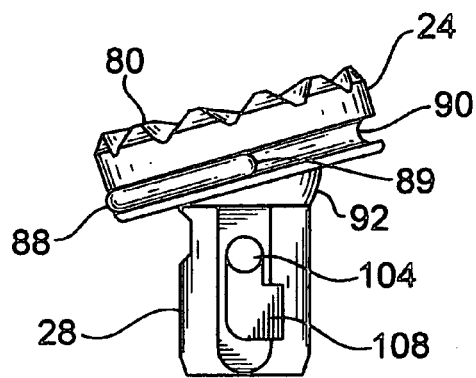
FIG. 5 is a side elevation of a locking member and washer assembly.
Figure 6:
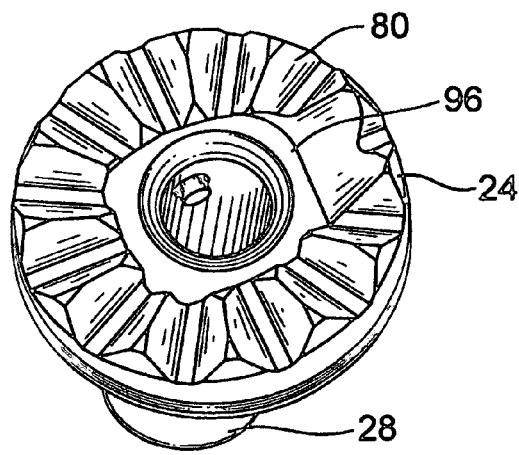
FIG. 6 is a perspective view.
Figure 7:
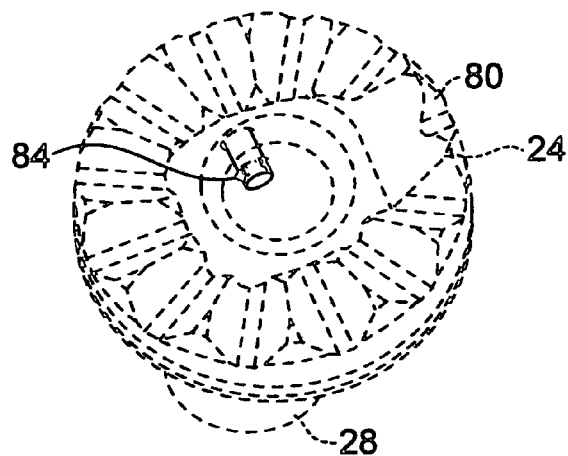
FIG. 7 is a perspective view, partially in phantom.
Figure 8:
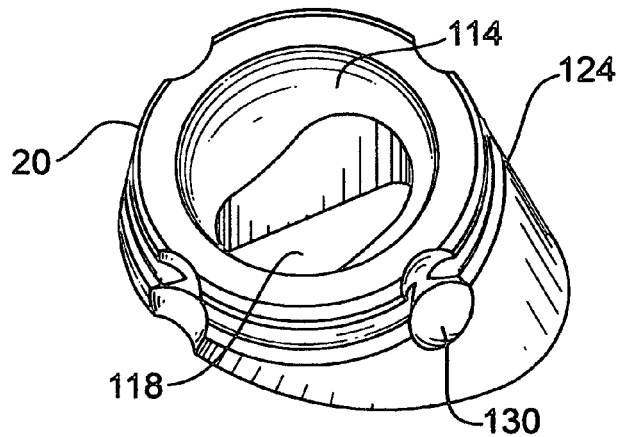
FIG. 8 is a perspective view of a first, superficial washer.
Figure 9:
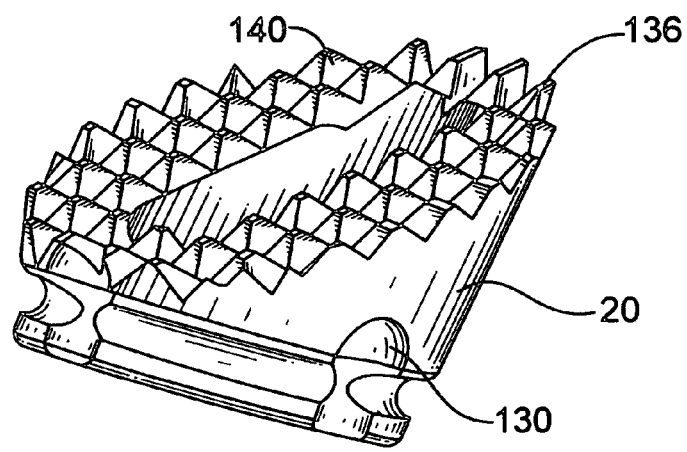
FIG. 9 is a bottom perspective view.
Figure 10:
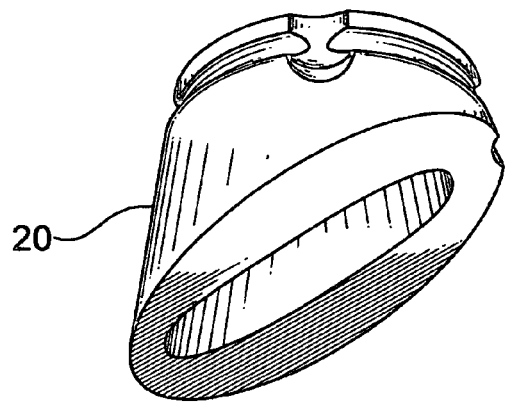
FIG. 10 is a bottom perspective view of an alternative embodiment.
Figure 11:
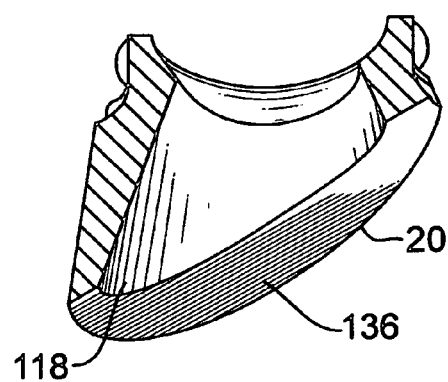
FIG. 11 is a bottom perspective view, partially broken away.

The second washer 24 and locking member 28 are shown in FIGS. 5-7. The second washer 24 can have suitable structure such as serrations 80 for engaging the bone surface. Alternative structure is possible. The second washer 24 is pivotal with respect to the locking member 28. The locking member 28 can have suitable structure such as apertures 84. Cooperating engagement structure such as clip 88 can be provided for extending through apertures 89 in the second washer 24 and engaging the apertures 84 such that the second washer 24 will engage the locking member 28. A convex surface 92 on the locking member 28 can cooperate with a similar concave surface 96 on the second washer 24. The clip 88 can be positioned in a suitable retaining groove 90 on the second washer 24. An aperture 104 and slotted L-shaped groove 108 can be provided to engage corresponding protrusions on the lower end portion 16 to secure the locking member 28 to the lower end portion 16 of the fastening device 10.

The first washer 20 is depicted in FIGS. 8-11. The first washer 20 can have a concave surface 114 for cooperating with the convex surface 54 of the head 48 of the fastener 44. An elongated opening 118, which can be in the form of a tapered slot, permits the pivoting of the first washer 20 relative to the fastener 44. The first washer 20 can have structure for allowing the washer to be engaged by the fastening device 10. This structure can be a circumferential groove 124 which can be engaged by cooperating flange structure on the fastening device 10. This will allow the first washer 20 to be advanced toward the surface of the bone. Additional structure such as depressions 130 can be provided for engagement by the fastening device 10 to permit rotation of the first washer 20. This will assist in properly positioning the first washer 20. The first washer 20 can have an angled contact surface 136 which will permit the first washer 20 to cooperate against bone surfaces such as facets which present significant angles. Additional structure can be provided for to promote engagement. This structure can include serrations 140 on the contact surface 136. The opening 118 can expand wider in a fluted manner toward the contact surface 136 to permit greater pivoting.

Figure 12A:
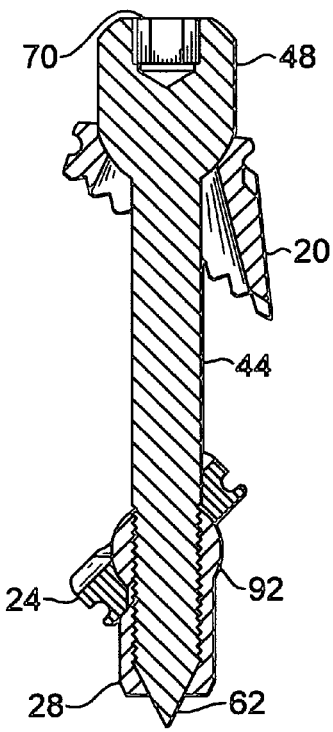
FIGS. 12a-c are cross-sectional views, partially broken away, showing alternative orientations.
Figure 12B:
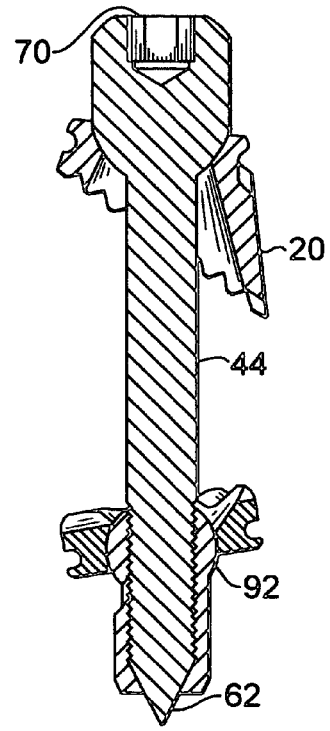
Figure 12C:
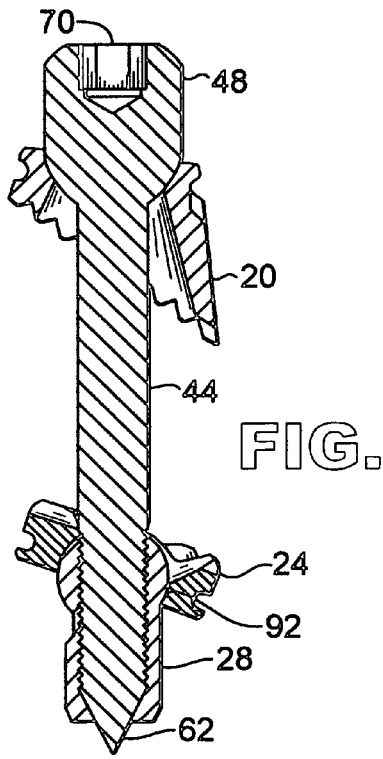

The manner of engagement between the fastener 44 and the first washer 20 and second washer 24 and locking member 28 is depicted in FIGS. 12a-c. The pivoting motion of the first washer 20 is shown. This washer can tilt approximately 30° from a transverse section through the screw axis. More or less is possible depending on the bone system that is being fused. The second washer 24 is capable of tilting +45° to −20° from the transverse to the screw axis. More or less is possible.

Figure 13:
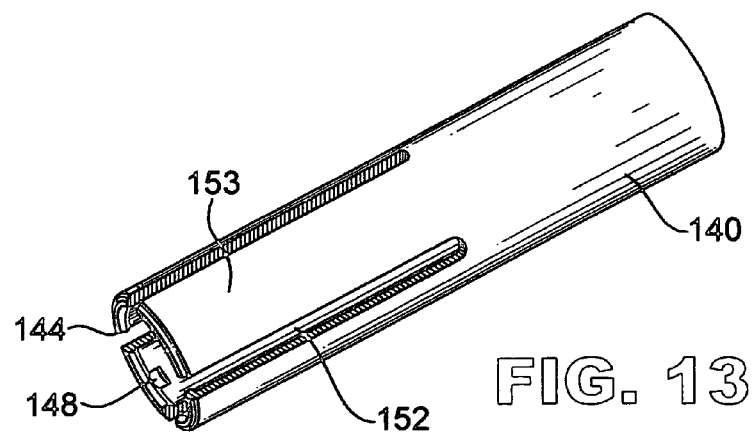
FIG. 13 is a perspective view of a collet.

Suitable structure can be provided with the fastening device 10 for engaging the first washer 20. There is shown in FIG. 13 a collet 140 although other holding structure is possible. The collet has distal circumferential flanges 144 which engage the groove 124 on the first washer 20. Protrusions 148 are provided to engage the depressions 130 to permit the rotation of the first washer 20. Elongated slots 152 provide leaf springs 153 for creating a spring action on the lower lips 144 such that the collet 140 can engage and disengage from the first washer 20 using moderate manual force.

Figure 14:
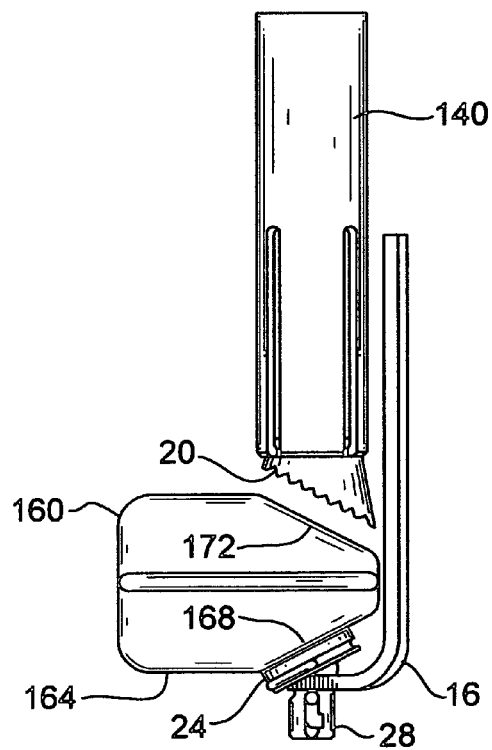
FIG. 14 is a schematic side elevation view showing a first mode of operation.
Figure 15:
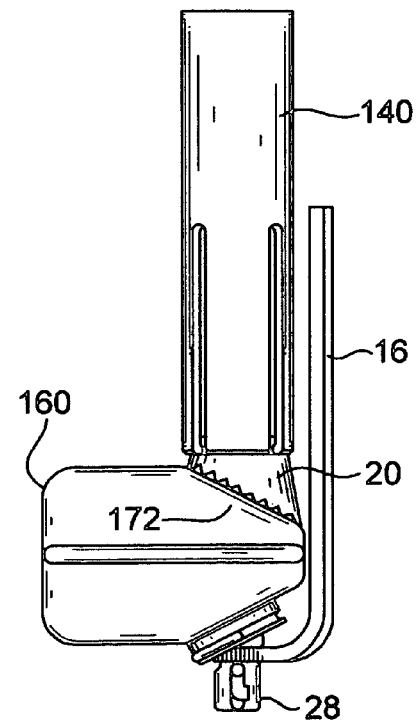
FIG. 15 is a schematic side elevation view showing a second mode of operation.

The manner of engaging the first washer 20 and second washer 24 to the bone is shown in FIGS. 14-15. The locking member 28 is engaged to the lower end portion 16 in a suitable slot. Protrusions in the lower end portion 16 can engage the apertures 104 in the locking member 28. The bone is shown schematically as a superior facet 160 and inferior facet 164. The first washer 20 is engaged to the collet 140. The lower end portion 16 is positioned such that the second washer 24 rests against the inferior facet 164. The pivoting of the lower washer 24 relative to the locking member 28 and lower end 16 permits the second washer 24 to match the incline portion 168 of the inferior facet 164. The collet 140 is then lowered such that the first washer 20 engages the incline portion 172 of the superior facet 160. The protrusions 148 engage the depressions 130 such that rotation of the collet 140 will rotate the first washer 20 to properly position the first washer 20 relative to the incline portion 172 of the superior facet 160.

Figure 16:
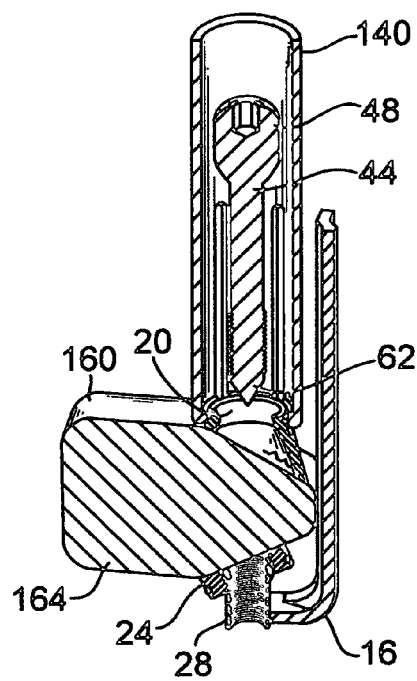
FIG. 16 is a schematic side elevation, partially broken away and partially in cross-section.
Figure 17:
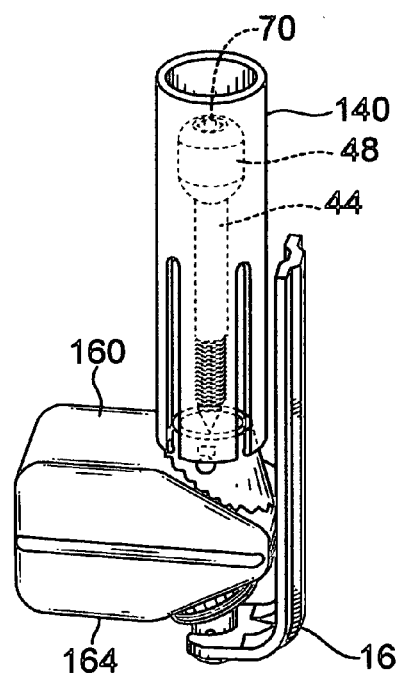
FIG. 17 is a schematic perspective view, partially broken away.
Figure 18:
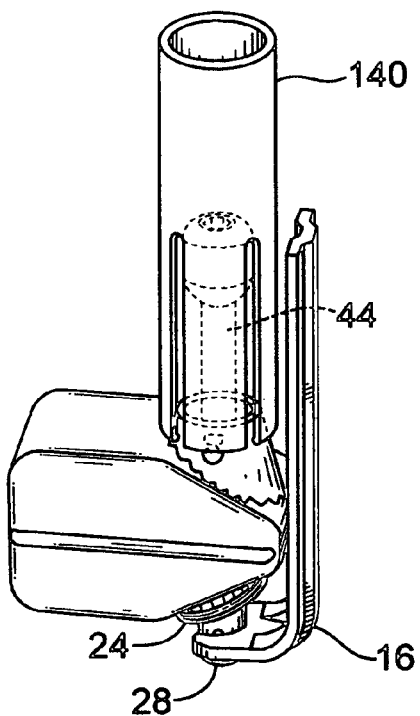
FIG. 18 is a schematic perspective view in a second mode of operation.
Figure 19:
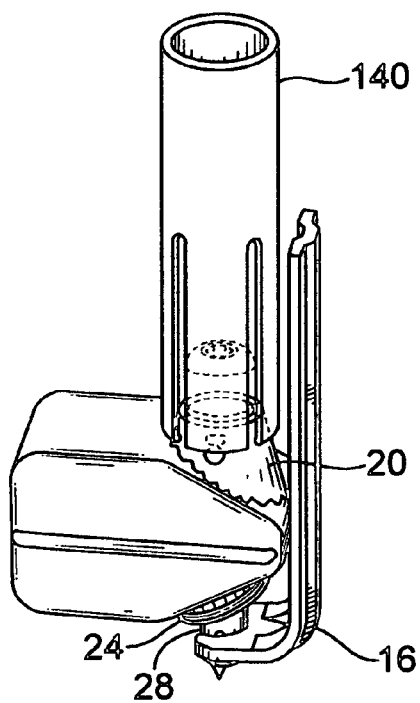
FIG. 19 is a schematic perspective view, partially in phantom, in a subsequent mode of operation.
Figure 20:
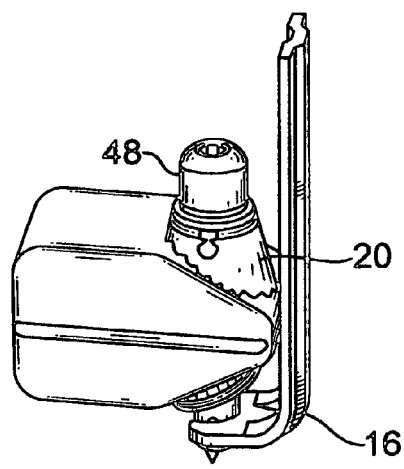
FIG. 20 is a schematic perspective view in yet another mode of operation.
Figure 21:
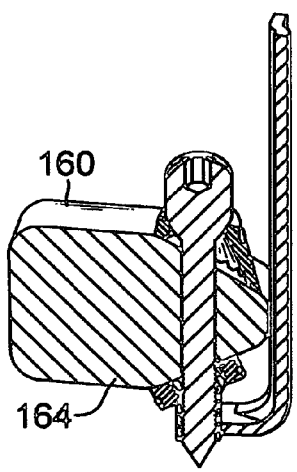
FIG. 21 is a schematic cross-sectional view.
Figure 22:
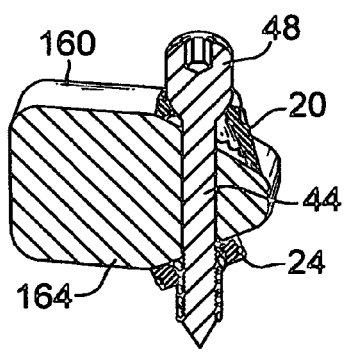
FIG. 22 is a schematic cross-sectional view illustrating a final installation.

The installation of the fastener 44 is shown in the sequence of FIGS. 16-18. The fastener 44 is held by a suitable engagement portion of the device 10 (not shown) and driven toward the superior facet 160. The fastener 44 can be engaged such that the head 48 can be rotated and the point 62 can be driven into the facet 160. Flutes can be provided on the pointed end 62 to remove bone debris as the fastener 44 is rotated and pushed into the bone. In this manner, the fastener 44 will drill through the superior facet 160 and inferior facet 164. As the fastener 44 is advanced through the bone, it will engage the locking member 28. The threads 58 will engage female threads in the locking member 28. The fastener 44 will thereby be engaged to the locking member 28, as shown in FIG. 19. The collet 140 can then be removed, as shown in FIGS. 20 and 21. The lower end portion 16 is then removed as the fastening device 10 is removed, as shown in FIG. 22. This results in a completed implant across the superior facet 160 and inferior facet 164, as shown in FIG. 23.

A bone fixation device 10 as used during an implantation procedure is illustrated in FIGS. 24-26. The device 10 has an elongated housing 14 in the general shape of a cannula. Within the housing is the collet 140. The collet 140 has structure for engaging the first washer 20. Any structure is possible, however, the collet 140 in FIG. 24 has inwardly directed circumferential holding flanges 144. The holding flanges 144 engage the groove 124 on the first washer 20. The collet 140 further can have protrusions 148 which engage the depressions 130 in the first washer 20. The first washer 20 is thereby held against movement out of the collet 140 and against rotation relative to the collet 140. The spring force holding the first washer 20 in the collet 140 is such that a manual force can be used to remove the collet 140 from the first washer 20 after the first washer 20 has been secured to the bone.

The collet 140 is mounted in the housing 14 so as to be axially movable therethrough. The collet 140 can have structure for slidably engaging a guide groove 222 or other suitable structure. The first trigger 34 can be operated to move the collet 140 and first washer 20 through the housing 14 from the position shown in FIG. 24 to the position shown in FIG. 25. When gear 230 is rotated the shaft 210 is pulled away by the threaded end of the shaft 246. The first washer 20 will be seated against the superior facet 160, and the second washer 24 will be seated against the inferior facet 164. The guide knob 35 can be rotated to properly position the second washer 24 if the orientation is not correct. The locking lever 32 can be operated to clamp the device to the facet.

The helical gear 230 is then rotated by the action of the trigger 38, which causes the mostly slidable hexagonal or flat faced shaft 210 to rotate. This rotates the extended threaded end of the shaft 246, which is engaged to mating internal threads 250 on an interior surface of the collet 140. The face of threaded end 246 includes structure for engaging the fastener 44, such as a hexagonal tip. Rotation of the threaded end 246 will thereby rotate and advance the fastener 44. The fastener 44 will advance through the first washer 20, and through the superior facet 160 and inferior facet 164 due to the drilling action created by the forward and rotational movement of the fastener 44. The fastener 44 will then advance through the second washer 24 and into the locking member 28. The threads 58 on the fastener 44 will engage cooperating threads on an inside surface of the locking member 28. The knob 37 can then be operated to properly torque the implant 40 including to fully seat fastener 44 with locking member 28.

The invention provides numerous advantages over prior art pedicle screw fixation systems. As the bone joint segments, such as the superior facet 160 and inferior facet 164, are compressed between the first washer 20 and second washer 24, there are no internal threads in the bone to raise stresses within the bone. The threads 58 are only on the lower end of the shaft 44 such that these threads engage only the locking member 28 and do not apply thread stresses to the interior of the bone. Also, as the implant is tightened using the rotational force, conventional torqueing mechanisms can be applied such that a known compressive force is applied to the joint. The first washer 20 and second washer 24 can be provided with varied angled contact surfaces to variously fit differing bone geometries for joining bone segments other than the facets. Also, the amount of tilt in the first washer 20 and second washer 24 relative to the fastener 44 can be adjusted depending upon the particular bone geometry that is being fused, owing to the pivotal and polyaxial motion that is permitted. The installation of the implant 40 is reversible. The compression of the implant washers 20 and 24 can be removed to allow repositioning prior to fastener 44 insertion. Accordingly, the invention provides great variability and flexibility, in addition to ease, control and consistency of installation.

The various components of the invention are constructed with constructions of surgical grade plastics or metal, such as titanium. Different dimensions of the various components of the invention are within the scope of the invention.

This invention can be embodied in other forms without departing from the spirit or essential attributes thereof and, accordingly, reference should be had to the following claims rather than the foregoing specification as indicating the scope of the invention.

We claim:

1. An implant for bone arthrodesis, comprising:
   a fastener with an elongated shaft having a head at one end and a threaded portion at the opposite end terminating in a bone-piercing point;
   a first washer having structure for engaging the head of said shaft so as to be polyaxially pivotable with respect to said head; and a locking member comprising a nut having threads that cooperate with the threaded portion on said shaft, said locking member having a second washer pivotally engaged thereto by a clip.

2. A system for performing bone fixation, comprising:

an implant for bone fixation, comprising a fastener with an elongated shaft having a head at one end and a bone-piercing point at the opposite end; a first washer having a first structure for engaging the head of said shaft so as to be polyaxially pivotable with respect to said head; and a locking member having a second structure for engaging said shaft, said locking member having a second washer pivotally engaged thereto:

a bone fixation device, comprising an elongated cannula having a collet for detachably engaging said first washer and for advancing the first washer, and a third structure for engaging said fastener and for advancing the fastener through the collet and through the first washer;

said bone fixation device further comprising a lower end portion extending from said cannula, said lower end portion having a fourth structure for detachably engaging said locking member, said fastener, first washer, and locking member being aligned such that said advancing fastener will advance through said first washer, through said bone, and into said locking member.

3. A method for performing bone fixation, comprising the steps of:

providing an implant for bone fixation, comprising a fastener with an elongated shaft having a head at one end and a bone-piercing point at the opposite end; a first washer having a first structure for engaging the head of said shaft so as to be polyaxially pivotable with respect to said head; and a locking member having a second structure for engaging said shaft, said locking member having a second washer pivotally engaged thereto;

providing a bone fixation device, comprising an elongated cannula having a collet for detachably engaging said first washer and for advancing the first washer, and a third structure for engaging said fastener and for advancing the fastener through the collet and through the first washer; a lower end portion extending from said cannula, said lower end portion having a fourth structure for detachably engaging said locking member, said fastener, first washer, and locking member being aligned such that said advancing fastener will advance through said first washer, through said bone, and into said locking member;

positioning said bone fixation device with said bone between said cannula and said lower end portion;

operating said device to advance said first washer to said bone; and operating said device to advance said fastener through said first washer, said bone, and said locking member.

4. A system for performing bone fixation, comprising:

an implant for bone fixation, comprising a fastener with an elongated shaft having a head at one end and a bone-piercing point at the opposite end; a first washer having a first structure for engaging the head of said shaft; and a locking member having a second structure for engaging said shaft;

a bone fixation device, comprising an elongated cannula having a third structure for detachably engaging said first washer and for advancing the first washer, and a fourth structure for engaging said fastener and for advancing and rotating the fastener through the first washer;

said bone fixation device further comprising a lower end portion extending from said cannula, said lower end portion having a fifth structure for detachably engaging said locking member, said fastener, first washer, and locking member being aligned such that said advancing fastener will advance through said first washer, drill through said bone, and advance into said locking member.

5. The system for performing bone fixation of claim 4, wherein said elongated cannula is detachable from said bone fixation device, whereby a replacement cannula having another implant can be attached to said device.

6. A method for performing bone fixation, comprising:

providing an implant for bone fixation, comprising a fastener with an elongated shaft having a head at one end and a bone-piercing point at the opposite end;

a first washer having a first structure for engaging the head of said shaft; and a locking member having a second structure for engaging said shaft;

providing a bone fixation device, comprising an elongated cannula having a third structure for detachably engaging said first washer and for advancing the first washer, and a fourth structure for detachably engaging said fastener and for advancing and rotating the fastener through the first washer;

said bone fixation device further comprising a lower end portion extending from said cannula, said lower end portion having a fifth structure for detachably engaging said locking member, said fastener, first washer, and locking member being aligned such that said advancing fastener will advance through said first washer, and advance into said locking member;

positioning said bone fixation device with said bone between said cannula and said lower end portion;

operating said device to advance said first washer to said bone; and operating said device to advance and rotate said fastener through said washer, drill through said bone, and move into said locking member.

* * * * *